United States Patent [19]

Kimock et al.

[11] Patent Number: 5,756,557

[45] Date of Patent: May 26, 1998

[54] AMINOMETHYL PYRROLIDINE UREA COMPOSITIONS FOR THE PRODUCTION OF POLYURETHANES

[75] Inventors: Michael John Kimock; Mark Leo Listemann, both of Kutztown, Pa.

[73] Assignee: Air Products and Chemicals, Inc., Allentown, Pa.

[21] Appl. No.: 851,652

[22] Filed: May 6, 1997

[51] Int. Cl.$^6$ ..................................................... C08G 18/20
[52] U.S. Cl. ........................... 521/129; 521/163; 528/49; 528/53; 528/73; 548/515; 548/567; 502/167
[58] Field of Search ........................ 528/49, 53, 73; 521/129, 163; 548/515, 567; 502/167

[56] References Cited

U.S. PATENT DOCUMENTS

| | | | |
|---|---|---|---|
| 4,007,140 | 2/1977 | Ibbotson | 260/2.5 AC |
| 4,094,827 | 6/1978 | McEntire | 260/2.5 AC |
| 4,194,069 | 3/1980 | Speranza et al. | 521/129 |
| 4,330,656 | 5/1982 | Grogler et al. | 528/52 |
| 4,644,017 | 2/1987 | Haas et al. | 521/129 |

FOREIGN PATENT DOCUMENTS

| | | |
|---|---|---|
| 2061168 | 8/1918 | Canada. |
| 3027796 | 2/1918 | Germany. |

*Primary Examiner*—Rachel Gorr
*Attorney, Agent, or Firm*—Michael Leach

[57] ABSTRACT

A method for preparing a polyurethane foam which comprises reacting an organic polyisocyanate and a polyol in the presence of a blowing agent, a cell stabilizer and a catalyst composition comprising a compound represented by the following formula I or II, or any blend of compounds I and II.

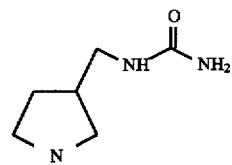

I

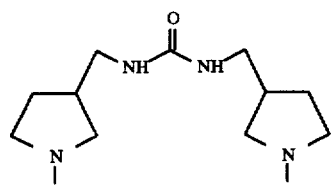

II

14 Claims, No Drawings

AMINOMETHYL PYRROLIDINE UREA COMPOSITIONS FOR THE PRODUCTION OF POLYURETHANES

BACKGROUND OF THE INVENTION

The present invention relates to the use of tertiary amine catalysts for producing polyurethanes, especially polyurethane foam.

Polyurethane foams are widely known and used in automotive, housing and other industries. Such foams are produced by reaction of a polyisocyanate with a polyol in the presence of various additives. One such additive is a chlorofluorocarbon (CFC) blowing agent which vaporizes as a result of the reaction exotherm, causing the polymerizing mass to form a foam. The discovery that CFCs deplete ozone in the stratosphere has resulted in mandates diminishing CFC use. Production of water-blown foams, in which blowing is performed with $CO_2$ generated by the reaction of water with the polyisocyanate, has therefore become increasingly important. Tertiary amine catalysts are typically used to accelerate blowing (reaction of water with isocyanate to generate $CO_2$) and gelling (reaction of polyol with isocyanate).

The ability of the tertiary amine catalyst to selectively promote either blowing or gelling is an important consideration in selecting a catalyst for the production of a particular polyurethane foam. If a catalyst promotes the blowing reaction to a too high degree, much of the $CO_2$ will be evolved before sufficient reaction of isocyanate with polyol has occurred, and the $CO_2$ will bubble out of the formulation, resulting in collapse of the foam. A foam of poor quality will be produced. On the other hand, if a catalyst too strongly promotes the gelling reaction, a substantial portion of the $CO_2$ will be evolved after a significant degree of polymerization has occurred. Again, a poor quality foam, this time characterized by high density, broken or poorly defined cells, or other undesirable features, will be produced.

Tertiary amine catalysts generally are malodorous and offensive and many have high volatility due to low molecular weight. Release of tertiary amines during foam processing may present significant safety and toxicity problems, and release of residual amines from consumer products is generally undesirable.

Amine catalysts which contain ureido functionality (e.g., $CONH_2$) have an increase in molecular weight and hydrogen bonding with reduced volatility and odor when compared to related structures which lack this functionality. Furthermore, catalysts which contain ureido functionality chemically bond into the urethane during the reaction and are not released from the finished product. Catalyst structures which embody this concept are typically of low to moderate activity and promote both the blowing (water-isocyanate) and the gelling (polyol-isocyanate) reactions to varying extents.

U.S. Pat. No. 4,644,017 discloses the use of certain diffusion stable amino alkyl ureas having tertiary amino groups in the production of a polyisocyanate addition product which do not discolor or change the constitution of surrounding materials such as PVC.

U.S. Pat. No. 4,007,140 discloses the use of N,N'-bis(3-dimethylaminopropyl)urea as a low odor catalyst for the manufacture of polyurethanes.

U.S. Pat. No. 4,194,069 discloses the use of N-(3-dimethylaminopropyl)-N'-(3-morpholinopropyl)urea, N,N'-bis(3-dimethylaminopropyl)urea and N,N'-bis(3-moroholinopropyl)urea as catalysts for producing polyurethanes.

U.S. Pat. No. 4,094,827 discloses the use of certain alkyl substituted ureas which provide lower odor and a delay in the foaming reaction that aids in the production of polyurethane foam.

U.S. Pat. No. 4,330,656 discloses the use of N-alkyl ureas as catalysts for the reaction of 1,5-napthylene diisocyanate with polyols or for the chain extension of prepolymers based upon 1,5-napthylene diisocyanate without accelerating atmospheric oxidation.

DE 30 27 796 A1 discloses the use of higher molecular weight dialkyl aminoalkyl ureas as reduced odor catalysts for the production of polyurethane foam.

CA 2,061,168 A (EP 0 499 873 A) discloses the preparation and use of pyrrolidines as catalysts for the polyisocyanate polyaddition process.

SUMMARY OF THE INVENTION

The present invention provides a composition for catalyzing the trimerization of an isocyanate and/or the reaction between an isocyanate and a compound containing a reactive hydrogen, e.g., the blowing reaction and the urethane reaction for making polyurethane. The catalyst composition comprises an aminomethyl pyrrolidine urea represented by formula I or II:

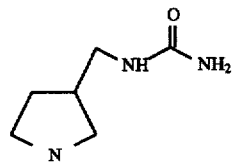

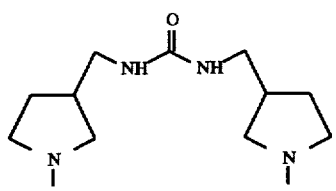

The catalyst composition may comprise compound I, compound II, or a blend of compounds I and II in any weight ratio.

The advantage of these catalyst compounds is their high activity and gelling selectivity. Additionally, they contain a ureido group which will react with isocyanate and chemically bond into the urethane during the reaction; therefore, the catalyst compound is not released from the finished product. The compositions are somewhat viscous and have minimal odor.

DETAILED DESCRIPTION OF THE INVENTION

The catalyst compositions according to the invention can catalyze (1) the reaction between an isocyanate functionality and an active hydrogen-containing compound, i.e. an alcohol, a polyol, an amine or water, especially the urethane (gelling) reaction of polyol hydroxyls with isocyanate to make polyurethanes and also the blowing reaction of water with isocyanate to release carbon dioxide for making foamed polyurethanes, and/or (2) the trimerization of the isocyanate functionality to form polyisocyanurates.

The polyurethane products are prepared using any suitable organic polyisocyanates well known in the art including, for example, hexamethylene diisocyanate, phenylene diisocyanate, toluene diisocyanate ("TDI") and 4,4'-diphenylmethane diisocyanate ("MDI"). Especially suitable are the 2,4- and 2,6-TDI's individually or together as their commercially available mixtures. Other suitable isocyanates are mixtures of diisocyanates known commercially as "crude MDI", also known as PAPI, which contain about 60% of 4,4'-diphenylmethane diisocyanate along with other isomeric and analogous higher polyisocyanates. Also suitable are "prepolymers" of these polyisocyanates comprising a partially prereacted mixture of a polyisocyanate and a polyether or polyester polyol.

Illustrative of suitable polyols as a component of the polyurethane composition are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols; for example, among others, ethylene glycol, propylene glycol, 1,3-butane diol, 1,4-butane diol, 1,6-hexane diol, neopentyl glycol, diethylene glycol, dipropylene glycol, pentaerythritol, glycerol, diglycerol, trimethylol propane and like low molecular weight polyols.

In the practice of this invention, a single high molecular weight polyether polyol may be used. Also, mixtures of high molecular weight polyether polyols such as mixtures of di- and trifunctional materials and/or different molecular weight or different chemical composition materials may be used.

Useful polyester polyols include those produced by reacting a dicarboxylic acid with an excess of a diol, for example, adipic acid with ethylene glycol or butanediol, or reacting a lactone with an excess of a diol such as caprolactone with propylene glycol.

In addition to the polyether and polyester polyols, the masterbatches, or premix compositions, frequently contain a polymer polyol. Polymer polyols are used in polyurethane foam to increase the foam's resistance to deformation, i.e. to increase the load-bearing properties of the foam. Currently, two different types of polymer polyols are used to achieve load-bearing improvement. The first type, described as a graft polyol, consists of a triol in which vinyl monomers are graft copolymerized. Styrene and acrylonitrile are the usual monomers of choice. The second type, a polyurea modified polyol, is a polyol containing a polyurea dispersion formed by the reaction of a diamine and TDI. Since TDI is used in excess, some of the TDI may react with both the polyol and polyurea. This second type of polymer polyol has a variant called PIPA polyol which is formed by the in-situ polymerization of TDI and alkanolamine in the polyol. Depending on the load-bearing requirements, polymer polyols may comprise 20–80% of the polyol portion of the masterbatch.

Other typical agents found in the polyurethane foam formulations include chain extenders such as ethylene glycol and butanediol; crosslinkers such as diethanolamine, diisopropanolamine, triethanolamine and tripropanolamine; blowing agents such as water, CFCs, HCFCs, HFCs, pentane and the like; and cell stabilizers such as silicones.

A general polyurethane flexible foam formulation having a 1–3 lb/ft$^3$ (16–48 kg/m$^3$) density (e.g., automotive seating) containing a gelling catalyst such as the catalyst composition according to the invention and a blowing catalyst such as bis(dimethylaminoethyl) ether (BDMAEE) would comprise the following components in parts by weight (pbw):

| Flexible Foam Formulation | pbw |
|---|---|
| Polyol | 20–100 |
| Polymer Polyol | 80–0 |
| Silicone Surfactant | 1–2.5 |
| Blowing Agent | 2–4.5 |
| Crosslinker | 0.5–2 |
| Catalyst | 0.2–2 |
| Isocyanate Index | 70–115 |

The gelling catalyst composition comprises a compound represented by formula I or II and any wt % combination of compounds I and II. Mixtures of compounds I and II may comprise 50 to 95 wt % compound I and 5 to 50 wt % compound II. As a result of the preparation procedure the catalyst composition may also contain up to 20 wt % unreacted urea III.

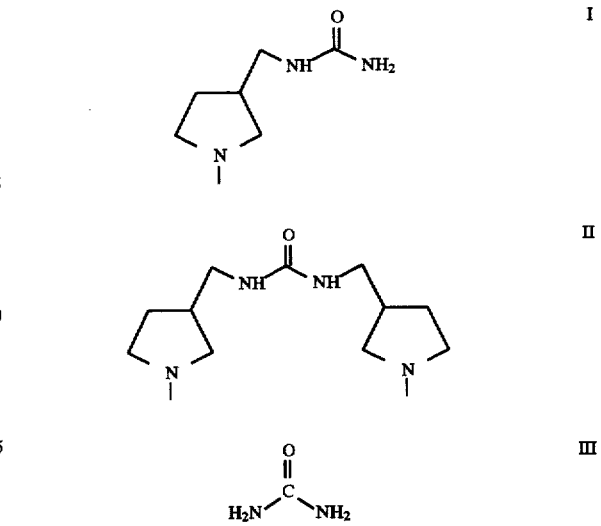

Compounds I and II are prepared by reacting urea and N-methyl-3-aminomethyl pyrrolidine in the appropriate molar ratios under an inert atmosphere at elevated temperatures. Compounds I and II can be isolated individually by chromatography.

Any blowing catalyst known in the polyurethane art may be used with the catalyst compounds of the invention. Illustrative of suitable blowing catalysts are BDMAEE, pentamethyldiethylenetriamine and related blends (U.S. Pat. No. 5,039,713), higher permethylated polyamines (U.S. Pat. No. 4,143,003), branched polyamines (U.S. Pat. No. 3,836,488), 2-[N-(dimethylaminoethoxyethyl)-N-methylamino] ethanol and related structures (U.S. Pat. No. 4,338,408), and alkoxylated polyamines (U.S. Pat. No. 5,508,314).

A catalytically effective amount of the catalyst composition is used in the polyurethane formulation. More specifically, suitable amounts of the catalyst composition may range from about 0.01 to 10 parts per 100 parts polyol (phpp) in the polyurethane formulation, preferably 0.1 to 1 phpp.

The catalyst composition may be used in combination with, or also comprise, other tertiary amine, organotin and carboxylate urethane catalysts (gelling and/or blowing) well known in the urethane art.

EXAMPLE 1

Blend of 1-(N-Methyl-3-pyrrolidino)methyl urea (I)
and 1,3-Bis(N-methyl-3-pyrrolidino)methyl urea
(II)

A one liter 3 neck round bottom flask was fitted with the following: mechanical stirrer, reflux condenser, nitrogen bubbler, and a temperature controlled heating mantle. The flask was charged with 45.75 g (0.762 mole) of urea ($CH_4N_2O$) and 86.84 g (0.762 mole) of N-methyl-3-aminomethyl pyrrolidine (IV), ($C_6H_{14}N_2$). Compound IV can be prepared according to Example 3 below.

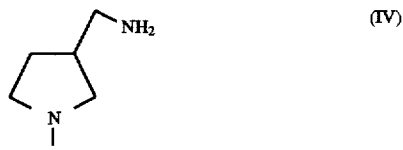 (IV)

The mixture was stirred at a constant rate while being slowly heated to 120° C. The reaction was controlled at 120° C. for two hours until all signs of $NH_3$ evolution had ceased (as evidenced by bubbling in the $N_2$ pressure relief device). The pale yellow liquid was cooled to 80° C. and the flask containing the liquid was evacuated via vacuum pump and refilled with $N_2$ three time to remove any volatiles still present. Quantitative $^{13}C$ NMR showed the product to be as follows in Table1.

TABLE 1

| Reaction Product Example 1 | mole % |
|---|---|
| 1-(N-Methyl-3-pyrrolidino)methyl urea (I) | 81.7 |
| 1,3-Bis(N-methyl-3-pyrrolidino)methyl urea (II) | 7.0 |
| Urea | 11.3 |

EXAMPLE 2

In this example a polyurethane foam was prepared in a conventional manner.

The polyurethane formulation in parts by weight (pbw):

| COMPONENT | PARTS |
|---|---|
| E-648 | 60 |
| E-519 | 40 |
| DC-5043 | 1.5 |
| Diethanolamine | 1.49 |
| Water | 3.5 |
| TDI 80 | 105 Index |

For each foam, the catalyst (Table 2) was added to 202 g of the above premix in a 32 oz (951 ml) paper cup and the formulation was mixed for 20 seconds at 5000 RPM using an overhead stirrer fitted with a 2 in (5.1 cm) diameter stirring paddle. Sufficient TDI 80 was added to make a 105 index foam [index=(mole NCO/mole active hydrogen)×100] and the formulation was mix well for 5 seconds using the same overhead stirrer. The 32 oz (951 ml) cup was dropped through a hole in the bottom of a 128 oz (3804 ml) paper cup placed on a stand. The hole was sized to catch the lip of the smaller cup. The total volume of the foam container was 160 oz (4755 ml). Foams approximated this volume at the end of the foam forming process. Maximum foam height and time to reach the top of the mixing cup (TOC1) and the top of the 128 oz. (3804 ml) cup (TOC2) were recorded (see Table 2).

TABLE 2

| CATALYST COMPOSITION | TOC1 (sec) | TOC 2 (sec) | Full Height (sec) | Foam Height (mm) |
|---|---|---|---|---|
| 0.25 pphp DABCO 33LV/ 0.10 pphp DABCO BL-11 | 12.88 | 39.14 | 132.60 | 420.79 |
| 0.48 pphp Ex 1 catalyst*/ 0.10 pphp DABCO BL-11 | 13.75 | 39.68 | 117.49 | 422.92 |

DABCO 33LV ® catalyst - 33 wt % TEDA in dipropylene glycol from Air Products and Chemicals, Inc.
DABCO BL-11 catalyst - 70 wt % BDMAEE in dipropylene glycol from Air Products and Chemicals, Inc.
*50 wt % Example 1 catalyst and 50 wt % dipropylene glycol.

The data in Table 2 show that the use of the Example 1 catalyst composition afforded a slower initial reactivity profile indicated by a longer TOC1, which improves flowability, followed by a shorter time to full rise, which indicates demold times would not be longer than that of the control. The Example 1 catalyst composition also has low odor and low volatility.

EXAMPLE 3

This procedure for making N-methyl-3-aminomethyl pyrrolidine is Example 1c of CA 2,061,168 A (EP 499 873 A).

A mixture of 300 g of N-methylglycine, 300 g of acrylonitrile, and 3 liters of toluene is introduced into a 4-liter three-necked flask equipped with stirrer, reflux condenser, dosing funnel, and a water separator having a capacity of about 70 ml. The mixture is heated at vigorous reflux at a bath temperature of from 120° to 140° C. A total of 105 g of paraformaldehyde is then added in portions of 3 g, with no portions being added until the evolution of water from the previous addition has ceased. A homogeneous, slightly yellowish solution is obtained at the end of the reaction. The solvent is distilled off and the residue is fractionated under vacuum to yield 315 g of N-methyl-3-cyanopyrrolidine (bp 83°–85° C., 22 mm Hg).

The subsequent reduction to N-methyl-3-aminomethyl pyrrolidine is carried out by dissolving the cyano compound in an equal volume of methanol. After the resultant solution is introduced into a 2 liter autoclave, 20 g of Raney cobalt is added and 130 g of ammonia is forced in. Hydrogenation is then carried out at 90° C. under a hydrogen pressure of from 90 to 100 bar for about 3 hours. The solution is depressurized, filtered, and concentrated by evaporation. The resultant residue is fractionated under vacuum to yield 310 g of N-methyl-3-aminomethyl pyrrolidine (bp 61° C., 22 mmbar).

STATEMENT OF INDUSTRIAL APPLICATION

The present invention provides a catalyst composition for preparing polyurethane products, especially polyurethane foams.

We claim:
1. 1-(N-methyl-3-pyrrolidino)methyl urea.
2. 1,3-Bis(N-methyl-3-pyrrolidino)methyl urea.
3. A catalyst composition comprising compound I or compound II, or a mixture of compounds I and II

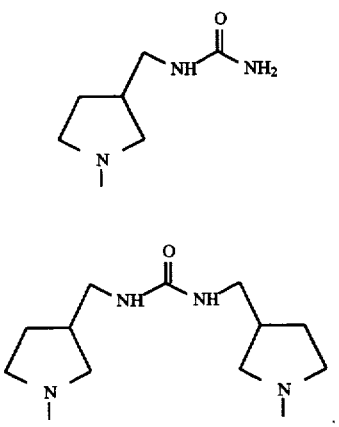

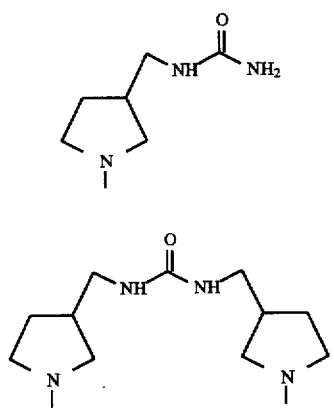

4. The catalyst composition of claim 3 which comprises

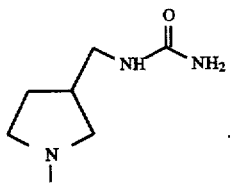

5. The catalyst composition of claim 3 which comprises

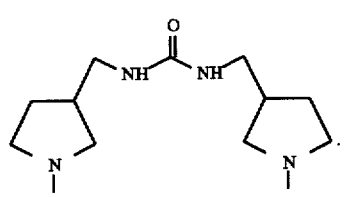

6. The catalyst composition of claim 3 which comprises a mixture of

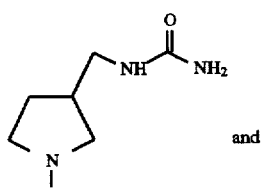

and

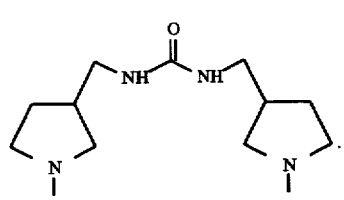

7. A method for catalyzing the trimerization of an isocyanatye and/or the reaction between an isocyanate and a compound containing a reactive hydrogen characterized by using a catalyst composition consisting essentially of compound I or compound II, or a mixture of compounds I and II 8. The method of claim 7 in which the catalyst composition comprises

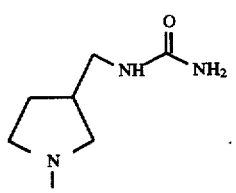

9. The method of claim 7 in which the catalyst composition comprises

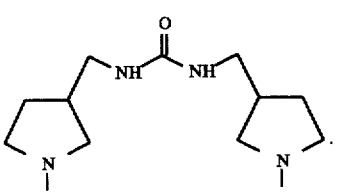

10. The method of claim 7 in which the catalyst composition comprises a mixture of

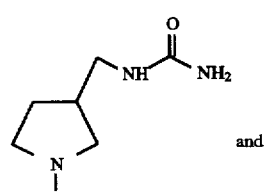

and

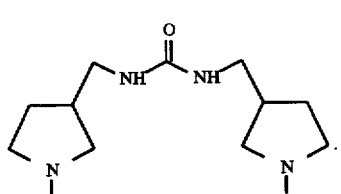

11. A method for preparing a polyurethane foam which comprises reacting an organic polyisocyanate and a polyol in the presence of a blowing agent, a cell stabilizer and a catalyst composition consisting essentially of compound I or compound II or a mixture of compounds I and II

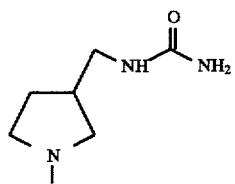
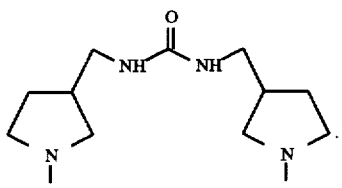
12. The method of claim 11 in which the catalyst composition comprises
14. The method of claim 11 in which the catalyst composition comprises a mixture of
13. The method of claim 11 in which the catalyst composition comprises
* * * * *